(12) United States Patent
Brace et al.

(10) Patent No.: US 6,187,005 B1
(45) Date of Patent: Feb. 13, 2001

(54) VARIABLE ANGLE SPINAL FIXATION SYSTEM

(75) Inventors: Michael Brace, Lansdale, PA (US); Eric Lange, Germantown, TN (US)

(73) Assignee: Synthes (USA), Paoli, PA (US)

( * ) Notice: Under 35 U.S.C. 154(b), the term of this patent shall be extended for 0 days.

(21) Appl. No.: 09/392,483

(22) Filed: Sep. 9, 1999

Related U.S. Application Data

(60) Provisional application No. 60/099,976, filed on Sep. 11, 1998.

(51) Int. Cl.[7] .................................................. A61B 17/56
(52) U.S. Cl. ................................................ 606/61; 606/73
(58) Field of Search ..................... 606/61, 72, 73

(56) References Cited

U.S. PATENT DOCUMENTS

| | | | |
|---|---|---|---|
| 4,946,458 | 8/1990 | Harms et al. | 606/61 |
| 5,047,029 | 9/1991 | Aebi et al. | 606/61 |
| 5,207,678 | 5/1993 | Harms et al. | 606/61 |
| 5,261,909 | 11/1993 | Sutterlin et al. | 606/61 |

(List continued on next page.)

FOREIGN PATENT DOCUMENTS

| | | |
|---|---|---|
| 195 09 332 C1 | 8/1996 | (DE) . |
| 0 330 881 A1 | 9/1989 | (EP) . |
| 0 465 158 A2 | 1/1992 | (EP) . |
| 2 759 894 | 8/1998 | (FR) . |
| WO 94/00066 | 1/1994 | (WO) . |
| WO 96/28104 | 9/1996 | (WO) . |
| WO 98/34554 | 8/1998 | (WO) . |

*Primary Examiner*—Michael Buiz
*Assistant Examiner*—Julian W. Woo
(74) *Attorney, Agent, or Firm*—Pennie & Edmonds LLP (57) ABSTRACT

A variable angle spinal fixation system is disclosed. The system includes a longitudinal member positionable along a spinal column, a fastener having a threaded end for engaging a vertebra, and a connector member for connecting the fastener and the longitudinal member. The connector member has a channel extending through side surfaces of the connector member for receiving the longitudinal member, an opening laterally displaced from the channel and extending through top and bottom surfaces of the connector member for receiving the fastener, and a fastener clamping element for securing the fastener in the opening at a surgeon selected angle relative to the connector member and longitudinal member. The system according to the present invention allows angulation of the fastener to accommodate complex pathologies.

12 Claims, 6 Drawing Sheets

U.S. PATENT DOCUMENTS

| | | | |
|---|---|---|---|
| 5,312,404 | * | 5/1994 | Asher et al. ............................ 606/61 |
| 5,312,405 | * | 5/1994 | Korotko et al. ........................ 606/61 |
| 5,352,226 | | 10/1994 | Lin .......................................... 606/61 |
| 5,466,237 | | 11/1995 | Byrd, III et al. ....................... 606/61 |
| 5,474,551 | | 12/1995 | Finn et al. .............................. 606/61 |
| 5,474,555 | | 12/1995 | Puno et al. .............................. 606/73 |
| 5,499,983 | | 3/1996 | Hughes ................................... 606/61 |
| 5,501,684 | | 3/1996 | Schlapfer et al. ...................... 606/73 |
| 5,520,690 | | 5/1996 | Errico et al. ........................... 606/61 |
| 5,527,314 | | 6/1996 | Brumfield et al. ..................... 606/61 |
| 5,531,746 | | 7/1996 | Errico et al. ............................ 606/61 |
| 5,549,608 | | 8/1996 | Errico et al. ............................ 606/61 |
| 5,554,157 | | 9/1996 | Errico et al. ............................ 606/61 |
| 5,575,791 | | 11/1996 | Lin .......................................... 606/61 |
| 5,575,792 | | 11/1996 | Errico et al. ............................ 606/61 |
| 5,578,033 | | 11/1996 | Errico et al. ............................ 606/61 |
| 5,584,831 | * | 12/1996 | McKay ................................... 606/61 |
| 5,584,834 | | 12/1996 | Errico et al. ............................ 606/61 |
| 5,586,984 | | 12/1996 | Errico et al. ............................ 606/61 |
| 5,591,166 | | 1/1997 | Bernhardt et al. ..................... 606/61 |
| 5,607,426 | | 3/1997 | Ralph et al. ............................ 606/61 |
| 5,609,593 | | 3/1997 | Errico et al. ............................ 606/61 |
| 5,609,594 | | 3/1997 | Errico et al. ............................ 606/61 |
| 5,613,968 | | 3/1997 | Lin .......................................... 606/61 |
| 5,643,259 | | 7/1997 | Sasso et al. ............................. 606/61 |
| 5,647,873 | | 7/1997 | Errico et al. ............................ 606/61 |
| 5,669,911 | | 9/1997 | Errico et al. ............................ 606/61 |
| 5,672,176 | | 9/1997 | Biedermann et al. .................. 606/61 |
| 5,683,392 | | 11/1997 | Richelsoph et al. ................... 606/61 |
| 5,688,273 | | 11/1997 | Errico et al. ............................ 606/61 |
| 5,690,630 | | 11/1997 | Errico et al. ............................ 606/61 |
| 5,728,098 | | 3/1998 | Sherman et al. ....................... 606/61 |
| 5,733,285 | | 3/1998 | Errico et al. ............................ 606/61 |
| 5,735,853 | | 4/1998 | Olerud .................................... 606/71 |
| 5,741,255 | | 4/1998 | Krag et al. .............................. 606/61 |
| 5,752,957 | | 5/1998 | Ralph et al. ............................ 606/61 |
| 5,776,135 | * | 7/1998 | Errico et al. ............................ 606/61 |
| 5,782,831 | | 7/1998 | Sherman et al. ....................... 606/61 |
| 5,797,911 | | 8/1998 | Sherman et al. ....................... 606/61 |
| 5,810,819 | | 9/1998 | Errico et al. ............................ 606/61 |
| 5,817,094 | | 10/1998 | Errico et al. ............................ 606/61 |
| 5,863,293 | | 1/1999 | Richelsoph ............................. 606/61 |
| 5,879,350 | | 3/1999 | Sherman et al. ....................... 606/61 |
| 5,938,663 | * | 8/1999 | Petreto ................................... 606/61 |
| 5,997,539 | * | 12/1999 | Errico et al. ............................ 606/61 |

* cited by examiner

VARIABLE ANGLE SPINAL FIXATION SYSTEM

This application claims benefit to U.S. provisional application Serial No. 60/099,976, filed Sep. 11, 1998.

FIELD OF THE INVENTION

The present invention is directed to a spinal fixation system, and in particular one which includes a variable angle spinal fixation device.

BACKGROUND OF THE INVENTION

Stabilization of the spine is often required following trauma, tumor, or degenerative pathologies. Although each region of the spine presents unique clinical challenges, posterior fixation of the cervical spine is particularly troublesome. The anatomy of the cervical spine makes it a technically challenging area to instrument. Specifically, several vital neural and vascular structures including the vertebral arteries, nerve roots, and spinal cord must be avoided during surgery.

Current methods of posterior cervical stabilization include the use of metallic wire or cable and plate/screw systems. Both wire and plating systems suffer from limitations. For example, in certain clinical applications such as occipital-cervical and cervical-thoracic pathologies, the fixed location of the plate screw holes makes alignment of the screws difficult and may comprise the achieved stabilization.

In order to alleviate the problems associated with fixed screw hole location, devices allowing variability in screw placement are available. For example, U.S. Pat. No. 5,735,852 discloses a clamp that can be placed anywhere along the length of a rod. One problem with this and similar designs is that the clamp has a screw hole surface oriented at a fixed angle with respect to the rod. As a result, these systems often do not provide sufficient angulation of the screw to accommodate complex degenerative pathologies.

Variable angle screw systems are also currently available. U.S. Pat. No. 5,549,608 discloses a polyaxial locking screw and coupling element device for use with a rod fixation apparatus. Because the rod is located on top of the screw after the device is assembled, the device disclosed in the '608 patent has a high profile and does not allow independent screw and rod fixation. Without independent screw and rod fixation, some adjustability is lost along with the ability to compress or distract along the rod. Furthermore, should one of the components loosen, the entire construct also loosens. The osteosynthetic fixation device disclosed in U.S. Pat. No. 5,501,684 requires that the rod be threaded through a channel rather than simply slipping the rod through an opening on the side or top of the device. It should also be noted that the devices of the '684 and '608 patents were designed for use in the lumbar and sacral regions of the spine.

U.S. Pat. No. 5,643,259 discloses spine fixation instrumentation for the cervical spine. Because the instrumentation disclosed in the '259 patent relies on a sleeve mechanism to secure the rod and the screw to the connector, it is difficult to align both sleeves with the connector. Furthermore, when several connectors are used, alignment is even more difficult and unintended distraction between levels may occur when joining the rod sleeves to the connectors. Due to the limited space between adjacent vertebrae in the cervical region of the spine, there may not be sufficient room between connectors to allow placement of the sleeves. In addition, optimal orientation of the '259 patent system is limited by the inability to rotate the screw about an axis parallel to the rod, i.e. the system only provides for two degrees of freedom, possibly resulting in the need to bend the rod in order for it to fit within the connector. Since the system of the '259 patent depends on the ability to slide the sleeve mechanism along the rod when securing the rod to the connector, the fact that the rod may have to be bent to account for the missing third degree of freedom may prohibit the proper functioning of this sleeve mechanism, and the rod may not lock securely. Finally, the assembly and disassembly processes are tedious and require complicated instruments.

As the discussion above illustrates, there is a need for an improved fixation apparatus for stabilizing the cervical spine.

SUMMARY OF THE INVENTION

The spinal fixation system according to the present invention comprises a longitudinal member positionable along a spinal column; a fastener having a threaded end for engaging a vertebra; and a connector member for connecting the fastener and the longitudinal member. The connector member includes a channel extending through side surfaces of the connector member for receiving the longitudinal member; an opening laterally displaced from the channel and extending through top and bottom surfaces of the connector member for receiving the fastener; and a fastener clamping element for securing the fastener in the opening at a surgeon selected angle relative to the connector member and longitudinal member. Preferably, the system further comprises a longitudinal member clamping element for securing the longitudinal member in the channel.

In one embodiment, the channel has a substantially oval-shaped cross section to allow positioning of the longitudinal member in the channel at discrete locations. In another embodiment, the channel is open on top to allow insertion of the longitudinal member in the channel. Alternatively, the channel is open on a side to allow insertion of the longitudinal member in the channel.

DESCRIPTION OF THE PREFERRED EMBODIMENTS

Figure 1:
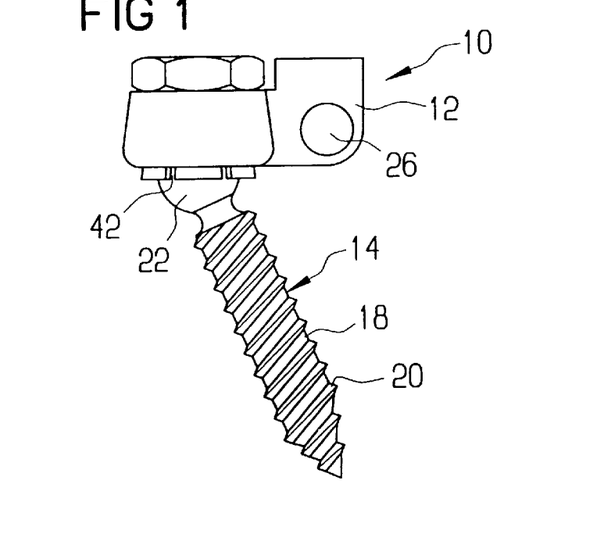
FIG. 1 is a side view of a first embodiment of the spinal fixation system according to the present invention.
Figure 2:
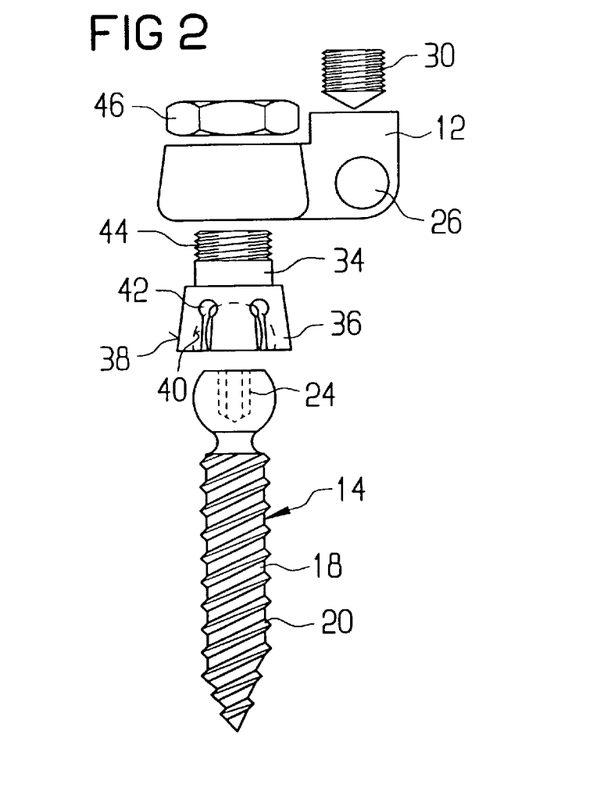
FIG. 2 is an exploded side view of the system of FIG. 1.

FIGS. 1 and 2 show a first embodiment of the spinal fixation system according to the present invention. Although the discussion of this and the other embodiments focuses on cervical fixation, it should be noted that the present invention can be used in other areas of the spine. System 10 includes a connector member 12 for connecting a fastener 14 to a rod 16 (seen best in FIG. 10). Usually at least two fasteners 14 and at least two corresponding connector members 12 are used with one rod 16. Fastener 14 has a stem 18 with a plurality of threads 20 and a hemispherical head 22 with a coupling 24 for attachment to a driver or other device for screwing fastener 14 into a vertebra. As described in more detail below, fastener 14 can be placed in the bone before the other components of system 10. This results in independent and optimal placement of fastener 14 according to the clinical situation, patient anatomy, and surgeon preference.

Connector member 12 has a channel 26 configured and dimensioned to receive rod 16. A threaded hole 28 (FIG. 3) intersects channel 26 so that when a set screw 30 is screwed into threaded hole 28, rod 16 is secured in channel 26. Connector member 12 has a tapered opening 32 (FIG. 3) for receiving cap 34. Cap 34 has a skirt 36 that has an exterior surface 38 tapered to closely match in size and shape tapered opening 32. An interior surface 40 of cap 34 is hemispherical to closely match in size and shape head 22 of fastener 14. Exterior surface 38 includes a plurality of slots 42 so that when head 22 is inserted into skirt 36, skirt 36 can flex outward until head 22 is flush with interior surface 40 at which point skirt 36 flexes back. Typically, correct insertion of head 22 into skirt 36 is determined by audible (i.e. a "click") and/or tactile feedback. Once head 22 is seated in skirt 36, head 22 and interior surface 40 function like a ball and socket joint so that fastener 14 can rotate about skirt 36.

The rotation freedom of fastener 14 allows for three dimensional variability of fastener 14 with respect to connector member 12 and rod 16. Thus, system 10 can be placed in any orientation that the surgeon desires to conform system 10 to patient anatomy. Another advantage of the rotation freedom is that fasteners 14 and connector members 12 can be connected without the need to contour, i.e. bend, rod 16. This simplifies the surgical procedure, reduces operating time, and prevents undue stress or damage to rod 16 caused by the bending.

Figure 3:
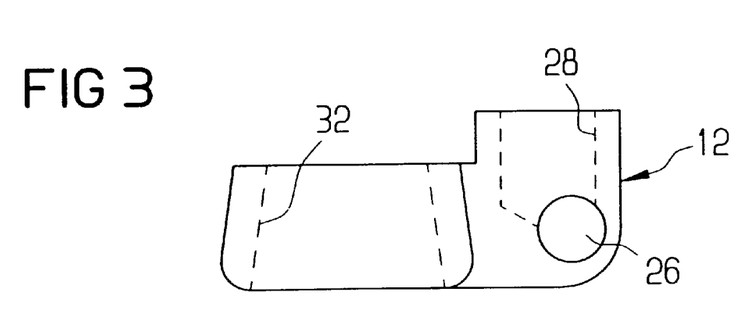
FIG. 3 is a side view of the connector member of FIGS. 1 and 2.

Cap 34 also has a threaded segment 44. When a nut 46 is screwed onto threaded segment 44, cap 34 is drawn into tapered opening 32. As cap 34 is drawn into tapered opening 32, the size of slots 42 is reduced and skirt 36 is compressed. The compression of skirt 36 secures head 22 in skirt 36 at a fixed position. Because fastener 14 and rod 16 are secured to connector member 12 by two separate mechanisms, fastener 14 can first be fixed to the vertebra at the desired location and angulation and then secured to connector member 12 before rod 16 is secured to connector member 12. The tightening of fastener 14 to connector member 12 prior to securing rod 16 allows compression or distraction of the vertebrae along rod 16 without sacrificing the optimal orientation of connector member 12 and fastener 14 already achieved. The separate tightening of fastener 14 to connector member 12 and rod 16 to connector member 12 also adds significant safety to system 10. This is due to the fact that both set screw 30 and nut 46 would have to loosen to completely destabilize system 10. In designs in which the rod sits on top of the screw, loosening of any of the stacked elements can result in failure of the entire implant. In further comparison to designs with the rod situated superior to the screw, laterally displacing fastener 14 with respect to rod 16 reduces the profile of system 10.

Figure 4:
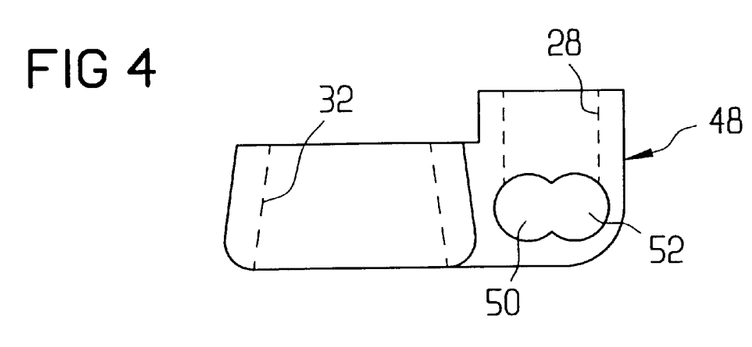
FIG. 4 is a side view of a connector member that allows a rod to be placed at two different positions in the connector member.

FIG. 4 shows another connector member 48 that can be used with system 10. Connector member 48 has two channels 50 and 52. Depending on the clinical application, rod 16 can be inserted in channel 50 or channel 52.

Figure 5:
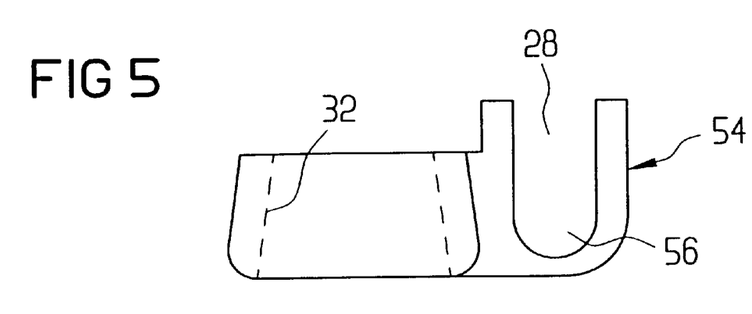
FIG. 5 is a side view of a top loading connector member.

FIG. 5 shows another connector member 54 that can be used with system 10. A channel 56 on connector member 54 is open on the top so that rod 16 can be inserted into channel 56 from the top. As was the case with connector member 12, a set screw (not shown) threaded into threaded hole 28 secures rod 16 to channel 56. The top loading design of connector member 54 facilitates inserting rod 16 into channel 56 after connector member 54 and fastener 14 are properly positioned. Because rod 16 is not obstructing the area around connector member 54, the top loading design also allows the surgeon to more easily pack the area around connector member 54 with bone graft or other osteoconductive material to enhance the formation of new bone.

Figure 6:
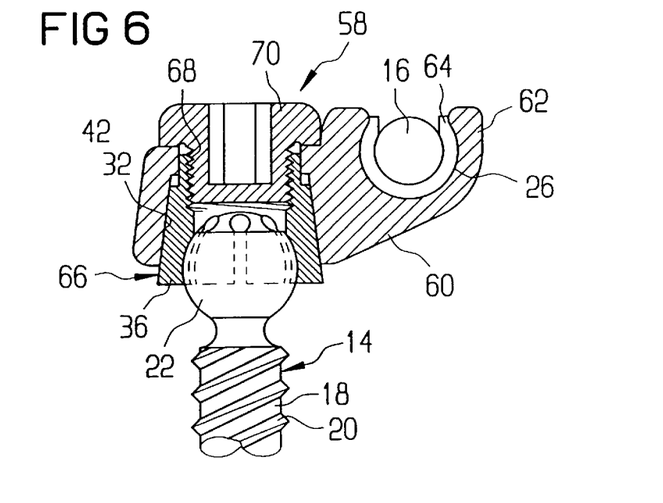
FIG. 6 is a cross sectional view of another embodiment of the spinal fixation system according to the present invention.

FIG. 6 shows another embodiment of a system 58 according to the present invention. System 58 has a connector member 60 which, like connector member 54, provides for top loading of rod 16. Connector member 60 includes a yoke 62 sized to receive a sleeve 64. As sleeve 64 is configured and dimensioned to cradle a portion of rod 16, inserted sleeve 64 into yoke 62 secures rod 16 to connector member 60. Any suitable sleeve design which securely fits in yoke 62 and tightly cradles rod 16 to connector member 60 can be used. An example of such a sleeve is the one disclosed in U.S. Pat. No. 5,643,259, the disclosure of which is incorporated herein by reference. A cap 66 of system 58 also differs from cap 34 of system 10. Cap 66 has internal threads 68 (rather than threaded segment 44) that mate with screw top 70 (rather than nut 46) to draw cap 66 into tapered opening 32.

Figure 7:
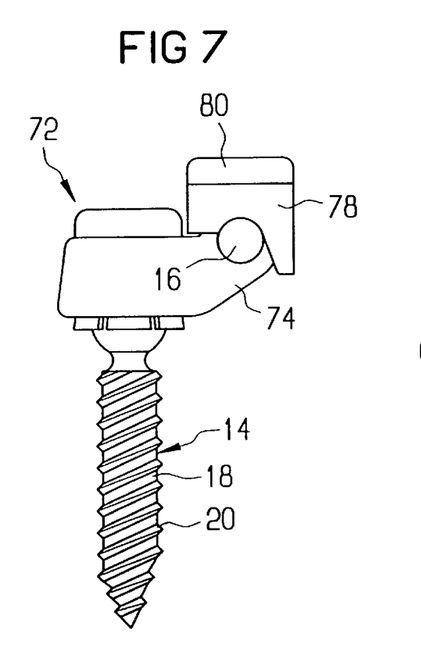
FIG. 7 is a side view of a different embodiment of the spinal fixation system according to the present invention.
Figure 8:
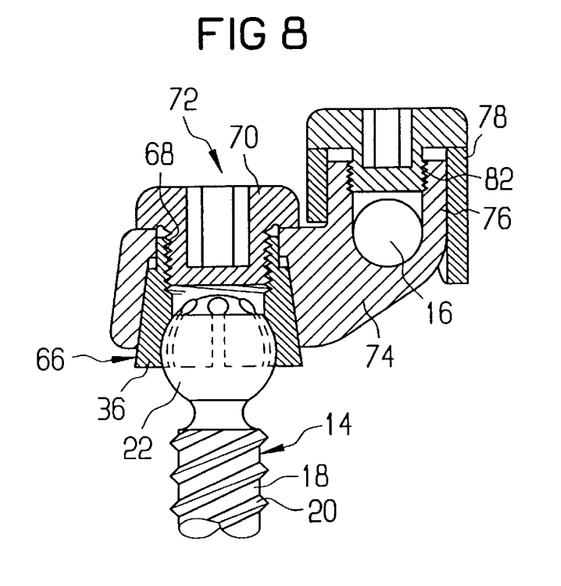
FIG. 8 is a cross sectional view of the system of FIG. 7.

FIGS. 7 and 8 show another embodiment of a top loading system 72 according to the present invention. A connector member 74 has a yoke 76 sized to accommodate rod 16. In order to secure rod 16 within channel 26, and in contrast to system 10 in which set screw 30 secures rod 16 in channel 26, in this embodiment a threaded top 80 mates with threaded walls 82 of yoke 76 to push an apron 78 against rod 16.

Figure 9:
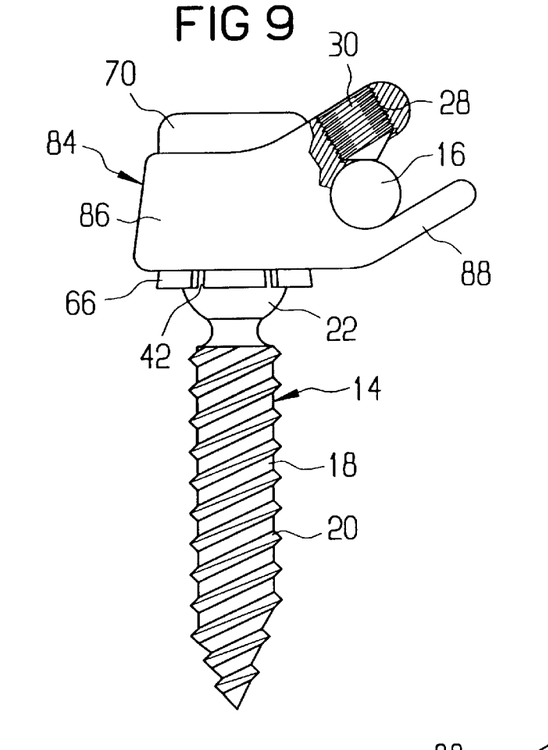
FIG. 9 is a side view of another embodiment of the spinal fixation system according to the present invention with a partial cross section.
Figure 10:
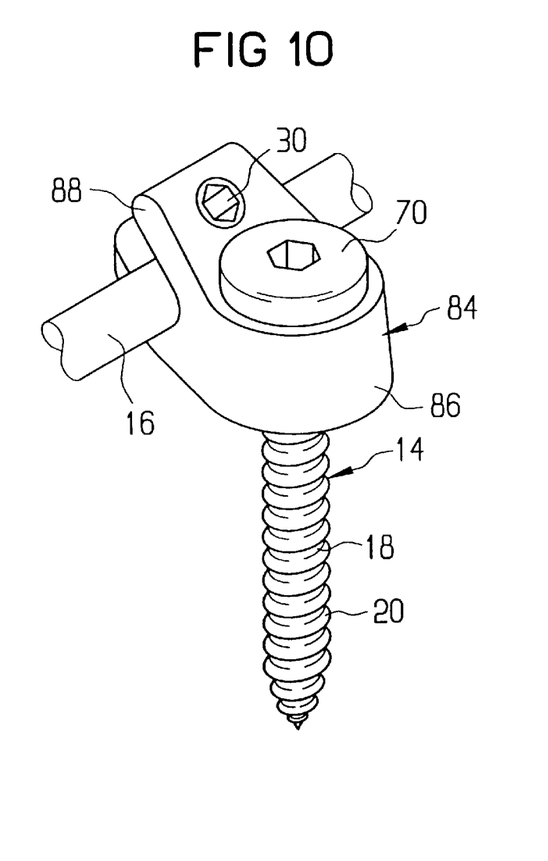
FIG. 10 is a plan view of the system of FIG. 9.

FIGS. 9 and 10 show another embodiment of a system 84 according to the present invention. System 84 is a side loading design, i.e. rod 16 slides into a connector member 86 from a side. Set screw 30 secures rod 16 to a yoke 88. The side loading design of connector member 86 facilitates inserting rod 16 to yoke 88 after connector member 86 and fastener 14 are properly positioned. Because rod 16 is not obstructing the area around connector member 86, the side loading design also allows the surgeon to more easily pack the area around connector member 86 with bone graft or other osteoconductive material to enhance the formation of new bone.

Figure 11:
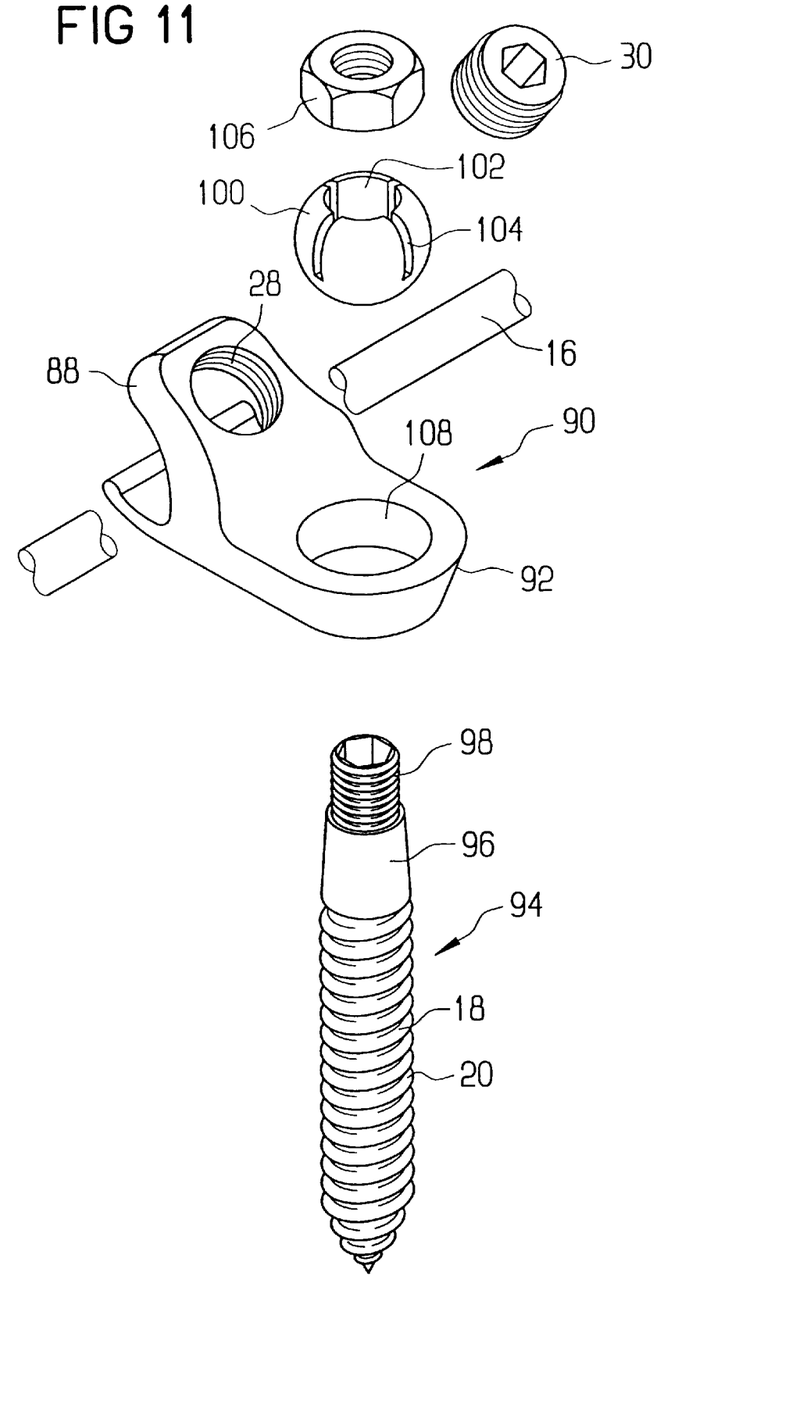
FIG. 11 is an exploded plan view of another embodiment of the spinal fixation system according to the present invention.

Another side loading system 90 with a connector member 92 is shown in FIG. 11. Rod 16, yoke 88, and the manner in which set screw 30 secures rod 16 to connector member 92 are identical to system 84 of FIGS. 9 and 10. However, fastener 94 is secured to connector member 92 using a ball clamp mechanism. Such a ball clamp mechanism is disclosed in U.S. Pat. No. 5,501,684, the disclosure of which is incorporated herein by reference. Fastener 94 has a stem 18 with a plurality of threads 20, and intermediate conical section 96, and a threaded cylindrical head 98. Ball clamp 100 has a conical bore hole 102 for receiving intermediate conical section 96 of fastener 94. Ball clamp 100 is shaped like a spherical shell and is provided with slits 104 to allow bore hole 102 to compress against intermediate section 96 upon the application of a compressive force. As a result, when a nut 106 is tightened on the threads of cylindrical head 98 with ball clamp 100 and intermediate section 96 inserted in a through hole 108, fastener 94 is secured to connector member 92.

Figure 12:
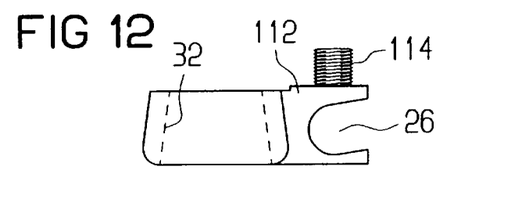
FIG. 12 is a side view of a side loading connector member.
Figure 13:
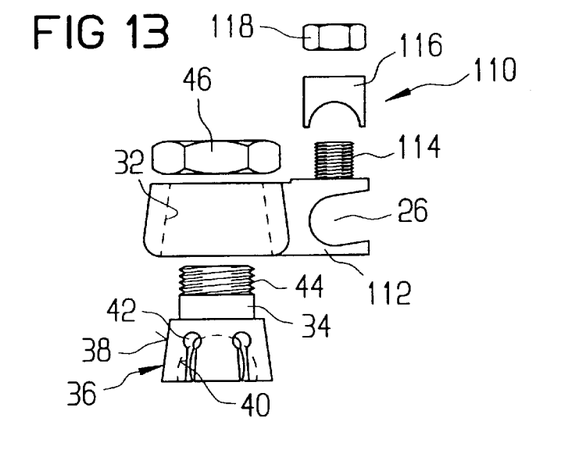
FIG. 13 is an exploded side view of the connector member of FIG. 12.

FIGS. 12 and 13 show another embodiment of a side loading system 110 according to the present invention. Connector member 112 is provided with a threaded stem 114 onto which an apron 116 slides to retain rod 16 in channel 26. A nut 118 fixes apron 116 to threaded stem 114.

Figure 14:
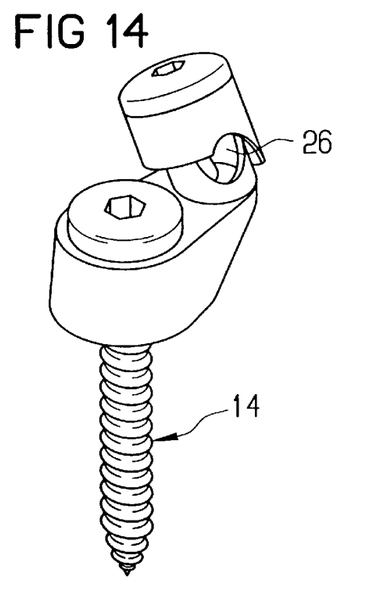
FIG. 14 is a plan view of a final embodiment of the spinal fixation system according to the present invention.
Figure 15:
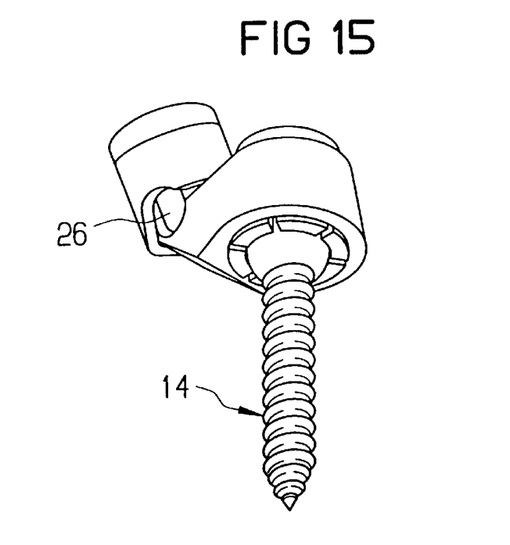
FIG. 15 is another plan view of the system of FIG. 14.

In all the embodiments described above and shown in FIGS. 1–13, the channel for the rod runs perpendicular to the opening for the fastener. However, as shown in FIGS. 14 and 15, channel 26 for rod 16 can be oriented at a non-orthogonal angle to opening 32 for fastener 14. This configuration is useful if angulation greater than that provided for by the fastener securing mechanism is desired. This is particularly useful for transarticular screw angulation requirements.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A spinal fixation system comprising:
    a longitudinal member positionable along a spinal column;
    a fastener having a threaded end for engaging a vertebra; and
    a connector member for connecting the longitudinal member and the fastener at any one of a plurality of surgeon selected angles obtained by pivoting the connector member with respect to the fastener, said connector member having:
        a channel extending through side surfaces of the connector member for receiving the longitudinal member;
        a longitudinal member clamping element for securing the longitudinal member in the channel;
        an opening laterally displaced from the channel and extending through top and bottom surfaces of the connector member for receiving the fastener; and
        a fastener clamping element for securing the fastener in the opening at the surgeon selected angle relative to the connector member and longitudinal member,
    wherein the channel is open to allow insertion and alignment of the longitudinal member with respect to the fastener prior to being secured by the longitudinal member clamping element.

2. The system of claim 1, wherein the channel has a substantially oval-shaped cross section to allow positioning of the longitudinal member in the channel at discrete locations.

3. The system of claim 1, wherein the channel is open on top to allow insertion of the longitudinal member in the channel.

4. The system of claim 3, wherein the longitudinal member clamping element comprises a sleeve with an interior surface configured and dimensioned to receive the longitudinal member and an exterior surface configured and dimensioned to fit securely within the channel.

5. The system of claim 1, wherein the channel is open on a side to allow insertion of the longitudinal member in the channel.

6. The spinal fixation system of claim 1 wherein the fastener has a threaded head and a non-threaded tapered cylindrical portion located between the threaded head and the threaded end.

7. The spinal fixation system of claim 6 further comprising a locking expansion element with top and bottom faces, a substantially hemispherical exterior surface, and a bore extending through the top and bottom faces, the bore having a taper matching the tapered cylindrical portion of the fastener.

8. The spinal fixation system of claim 7 wherein the opening of the connector member has a substantially hemispherical shape to accommodate the exterior surface of the locking expansion element.

9. The spinal fixation system of claim 8 further comprising a nut having a thread configured and dimensioned to mate with the threaded head of the fastener, wherein the nut bears against the top surface of the locking expansion element upon threading onto the threaded head of the fastener to thereby drive the locking expansion element over the tapered cylindrical portion of the fastener.

10. The spinal fixation system of claim 1 wherein the longitudinal member clamping element and fastener clamping element are separate components that operate independently.

11. The spinal fixation system of claim 1 wherein the connector member includes a yoke defining the channel.

12. A spinal fixation system comprising:
    a longitudinal member positionable along a spinal column;
    a fastener having a threaded end for engaging a vertebra; and
    a connector member for connecting the fastener and the longitudinal member, said connector member having:
        a channel extending through side surfaces of the connector member for receiving the longitudinal member, the channel open on top to allow insertion of the longitudinal member therein;
        a yoke defining the channel and having walls with threads;
        an apron slidable over the yoke walls for retaining the longitudinal member in the channel;
        a screw top having threads which mate with the yoke wall threads to secure the apron to the yoke walls
        an opening laterally displaced from the channel and extending through top and bottom surfaces of the connector member for receiving the fastener; and
        a fastener clamping element for securing the fastener in the opening at a surgeon selected angle relative to the connector member and longitudinal member.

* * * * *